United States Patent [19]
Ramon

[11] Patent Number: 5,085,227
[45] Date of Patent: Feb. 4, 1992

[54] CONDUCTIVE CUTANEOUS COATING FOR APPLYING ELECTRIC CURRENTS FOR THERAPEUTIC OR BEAUTY TREATMENT

[76] Inventor: Gérard Ramon, 31380 Montastruc-la-Conseillere, Gragnague, France

[21] Appl. No.: 480,613

[22] Filed: Feb. 15, 1990

[30] Foreign Application Priority Data

Feb. 15, 1989 [FR] France ................. 89 01949

[51] Int. Cl.$^5$ .............................................. A61N 1/18
[52] U.S. Cl. ..................................... 128/792; 128/802; 252/500
[58] Field of Search ................. 128/639–641, 128/798, 802, 803, 791, 792; 252/500

[56] References Cited

U.S. PATENT DOCUMENTS

| | | | |
|---|---|---|---|
| 3,265,638 | 8/1966 | Goodman et al. | 128/803 X |
| 3,565,059 | 2/1971 | Hauser et al. | 128/640 |
| 3,659,614 | 5/1972 | Jankelson | 128/791 |
| 3,881,495 | 5/1975 | Pannozzo et al. | 128/422 |
| 4,094,822 | 6/1978 | Kater | 128/640 X |
| 4,210,633 | 7/1980 | Takruri et al. | 424/80 |
| 4,317,457 | 3/1982 | Guillot | 128/783 |
| 4,367,745 | 1/1983 | Welage | 128/798 |
| 4,473,492 | 9/1984 | Schmolka | 128/803 X |
| 4,585,797 | 4/1986 | Cioca | 514/773 |
| 4,591,501 | 5/1986 | Cioca | 424/28 |

FOREIGN PATENT DOCUMENTS

| | | |
|---|---|---|
| 0004514 | 10/1979 | European Pat. Off. . |
| 0159167 | 10/1985 | European Pat. Off. . |
| 1589524 | 7/1970 | Fed. Rep. of Germany . |
| 3133434 | 3/1983 | Fed. Rep. of Germany ...... 128/639 |
| 2047874 | 3/1971 | France . |
| 2503561 | 10/1982 | France . |

OTHER PUBLICATIONS

Kobayashi Kose Co., Ltd., Chemical Abstracts, 1979, p. 332, vol. 91, 91:216679e.
A. Julien et al., "Les masques de beauté", Dec. 1986, pp. 61–64, No. 72.

Primary Examiner—Lee S. Cohen
Attorney, Agent, or Firm—Perry Carvellas

[57] ABSTRACT

A conductive cutaneous coating for application to an area of a person's skin for use in applying electric currents for therepeutic or beauty treatment comprises a gel polymerizable when brought into contact with air of a terniary mixture of polyvinyl alcohol, ethanol and water, and a plastifier physiologically acceptable for topical application. A generator lead has two conductors each connected to a conductive plate disposed at electrically insulated ends of a head clip, the conductive plates bearing against the mask through porous pads soaked with a saline solution at a location at the rear of the cheekbones at ear level.

17 Claims, 1 Drawing Sheet

CONDUCTIVE CUTANEOUS COATING FOR APPLYING ELECTRIC CURRENTS FOR THERAPEUTIC OR BEAUTY TREATMENT

BACKGROUND OF THE INVENTION

The invention relates to a conductive cutaneous sheet or coating for applying an electric current to a person's skin for therapeutic or beauty treatment, comprising a layer of a settable composition spread over an area of skin and having a substantial electrical conductivity during setting.

The invention also relates to an apparatus employing such a coating applied as a facial mask.

U.S. Pat. No. 4,317,457 discloses an electrically conductive casting defining a cutaneous electrode for applying electric current to parts of the human body for therapeutical or beauty purposes. The casting according to this reference comprises a powder, typically a dental quality powder, which is settable when mixed with an excess quantity of water containing a dissolved salt, typically calcium chloride. Metal contacts are embedded in the casting for applying electric current supplied by a generator. Normally a counterelectrode comprising another casting is employed. As the casting becomes practically nonconductive when it hardens, the current is applied before setting of the casting is completed.

In use it has been found that the preparation of the electrically conductive castings, applying them to the person's skin, and monitoring the application of electric current requires skilled and trained operators. Further, the person being treated must keep the part of his/her body immobile to which the casting is applied until the casting has attained sufficient mechanical strength.

Thus therapeutic and aesthetic treatments of the skin by means of electric currents must be performed in clinics or otherwise under the care of skilled practitioners.

It thus seemed desirable to develop cutaneous electrode which could be applied and used by the person to be treated in cases where treatment does not otherwise require the monitoring by a skilled practitioner.

According to the invention there is provided a conductive cutaneous coating for application to an area of a person's skin for use in applying electric currents for therapeutic or beauty treatment, said coating comprising a layer of a settable composition, spread over an area of skin and having substantial electrical conductivity during setting, the improvement wherein the composition is a gel polymerizable when brought into contact with air and comprises a terniary mixture of polyvinyl alcohol, ethanol and water, and a plastifier physiological acceptable for topical application.

The polymerization of the gel thus formed results in the formation of a flexible coating which is intimately applied to the skin and follows slight deformation thereof throughout polymerization. The coating has a conductivity of the same order of magnitude as cutaneous tissue until polymerization is completed, in conditions comparable to those of known electrically conductive castings. Upon completion of polymerization the coating is removed in one piece or large strips, without sticking to the skin.

Preferably, the composition comprises 15 to 30% polyvinyl alcohol having a degree of hydrolysis greater than 85%, 7 to 15 wt % ethanol, 1.5 to 3 wt % water-soluble lanolin, 0.7 to 1.5 wt % glycerol, and the remainder water.

The preferred composition comprises 20 wt % polyvinyl alcohol, 10 wt % ethanol, 2 wt % water-soluble lanoline, 1 wt % glycerol, the remainder being water.

Preferably, the amount of polyvinyl alcohol is adjusted together with the selection of the degree of condensation to obtain a gel viscosity between 2,000 and 3,000 Pa.s.

The preferred kind of polyvinyl alcohol has an ester index of about 70%, and a degree of condensation so that the viscosity of a 4 wt % aqueous solution is about 3 Pa.s at 20° C.

Concurrently with a gel capable of forming a conductive coating which the user can apply to his/her skin, it has also appeared desirable that the current generator be portable to enable the user to perform the treatment by himself or herself at home in cases where the actual treatment does not require the presence of a practitioner.

According to another aspect of the invention it is preferably for the treatment of large cutaneous areas to employ cutaneous electrodes having electrical conductivity parallel to the skin which is substantially that of the subjacent skin tissue. When applying voltage between two spaced points of the coating, the voltage gradients in the portions of the coating and the subjacent skin are similar. The treatment can be carried out by connecting two spaced points of the coating to the terminals of an appropriate generator. Thereupon it is unnecessary to use counter-electrodes for the return current or to form a gap in the coating to define a pair of electrodes. This is all the more so as the presence of such a gap between two coating portions has the tendency to produce relative large voltage gradients in the area of the gap and localized currents in this gap.

Thus the invention also provides an apparatus for cutaneous therapeutic or beauty treatment by applying pulsed electric current to facial skin, a conductive coating adapted to be applied as a facial mask, a lead connecting the conductive coating to the terminals of a generator, the improvement wherein the conductive coating comprises a one-piece facial mask of a gel polymerizable in contact with air and comprising 15 to 30 wt % polyvinyl alcohol having a degree of hydrolysis greater than 85%, 5 to 15 wt % ethanol, 1.5 to 3% water-soluble lanolin, 0.7 to 1.5 wt % glycerol, the remainder being water, the lead having two conductors each connected to a conductive plate disposed at electrically insulated ends of an arcuate head clip, the conductive plates bearing against the mask through porous pads soaked with a saline solution at a location at the rear of the cheekbones at ear level.

The combinations of the features of the apparatus participate in facilitating the nonprofessional application of the electrical currents for treatment.

These and other features and advantages will become apparent from the description which follows, given by way of example, of a preferred embodiment of the invention.

DETAILED DESCRIPTION OF THE PREFERRED EMBODIMENTS

Figure 1:
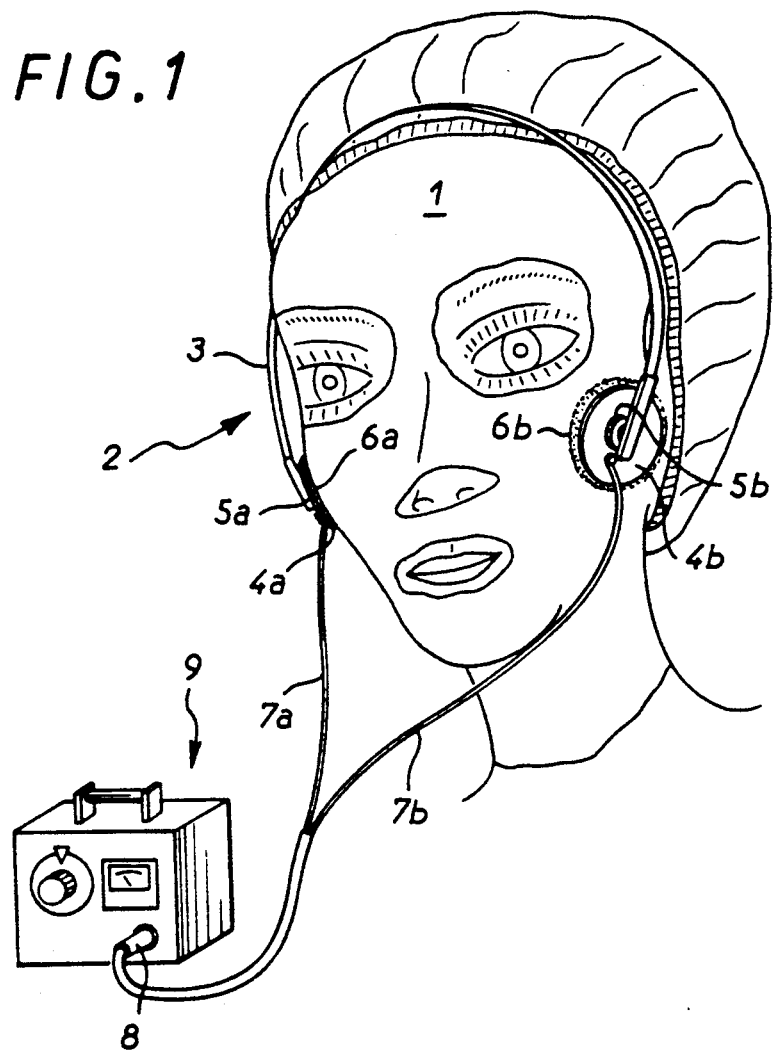
FIG. 1 illustrates a conductive coating according to the invention, forming a facial mask for electrical treatment, for use with a treatment apparatus.

According to the preferred embodiment illustrated in FIG. 1, a coating or sheet comprises a mask 1 formed in situ on a person's face, extending from the location immediately below the hairline to the base of the neck, with cutouts for the eyes, nostrils and mouth. The mask 1 is formed from a gel polymerizable in contact with air after application to the person's skin, and is conductive during polymerization. The composition of the gel will be given below.

Two contacts 4a, 4b fixed to the ends of a resilient arcuate head clip 3 are provided on the mask, insulating members 5a, 5b being interposed between the ends of the head clip 3 and the contacts 4a, 4b. The contacts 4a, 4b are located at the rear of the cheekbones substantially at ear level and bear against the mask through porous pads 6a, 6b which are conductive owing to their being soaked with a saline solution. Each of contacts 4a, 4b is contacted to the end of a corresponding conductor 7a, 7b which together form a lead 8 having a jack connecting the lead to a pulsed current generator 9. It will be noted the head unit 2 comprising the arcuate head clip 3, contacts 4a, 4b and the lead has a strong visual resemblance to headphones.

Figure 2:
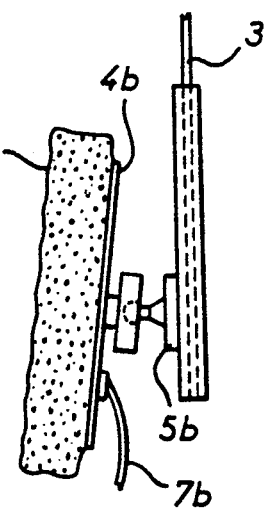
FIG. 2 is a detail view of an electrical connector for the conductive mask.

As best seen in FIG. 2, the ends of the arcuate head clip 3 are sheathed in insulation and equipped with an insulating ball member 5b swivelly engaging a complementary socket member which in turn is secured to a circular metal plate 4b to which the conductor 7b is connected. The metal plate 4b thus defines a contact to which is applied the pad or sponge member 6b. At the other hand of the head clip 3 is an insulating ball and socket member, a circular metal plate or contact 4a to which the other conductor 7a is connected, and a pad or sponge member 6a attached to the disc.

The current generator 9 supplies pulsed voltage having an adjustable voltage peaks and frequencies such as is known in the field of electrical therapeutic and beauty treatments. The shape and polarity of these pulses will not be described in detail herein, as they are known per se and outside the present invention. The peak voltage may reach 150 volts and the recurrent frequency is between 40 and 110 cycles/second.

The maximum effective current which the generator 9 can supply is about 2 mA, which is the current intensity corresponding to a treatment of a large skin area such as the bust. Owing to the reduced power requirement the generator 9 can be portable and by supplied by a 9-volt battery.

It will be noted that contacts 4a and 4b are fitted on the mask which comprises a single continuous layer. Thus the voltage applied by the contacts 5a, 5b will conduct the current directly to the mask itself and the subjacent cutaneous tissue. Although the current which flows in the mask constitutes a loss of energy, it establishes a voltage gradient between the contacts 4a, 4b. If the resistivities of the mask and the subjacent facial tissue are of the same order of magnitude, the stray currents in the mask are moderate, but the voltage distribution attenuates the occurrence of abnormal conductive zones in the cutaneous tissue.

Typically the composition by weight of the gel for the mask is as follows:

| | |
|---|---|
| Rhodoviol ® 30/70 polyvinyl alcohol | 20% |

-continued

| | |
|---|---|
| Ethanol | 10% |
| Glycerol | 1% |
| Water-soluble lanolin | .2% |
| Deionized water | remainder |

The resulting mixture has a viscosity at 20° C. of about 2,490 Pascals.second (24,900 centipoises) and a volumetric resistivity of 27.5 ohm.meters.

This mixture stored out of contact with air has rather stable properties and does not required any mixing of components.

On the other hand, when it is applied to in a layer to a person's skin, the gel very quickly becomes thicker and then it is usable as a conductive coating. After about a half hour, the polymerization is nearly completed and the electrical resistance is very high. The coating in the form of a mask can then be peeled off in one piece but remains flexible.

The gel composition is usable within tolerance of the ingredients of ±50%, the amount of water always being the remainder to 100%.

The speed of polymerization can be controlled by adjusting the amount of ethanol.

Various tests have been conducted with Rhodoviol® polyvinyl alcohols sold by Rhône-Poulenc, namely Rhodoviol 30/70
Rhodoviol 4/125
Rhodoviol 25/140

The numerator expresses the degree of condensation of the polyvinyl alcohol expressed as viscosity in centipoises (1 CP = 10 Pa.s) of the 4 wt % solution in water at 20° C. The denominator represents the degree of hydrolysis, expressed as an index of a conventional ester. The correspondence between the ester index and the degree of hydrolysis (in molecules per hundred) is given in the following table:

| Ester Index | Degree of Hydrolysis (Mol %) |
|---|---|
| 70 | 94% |
| 125 | 89% |
| 140 | 88% |

The best results were obtained with degrees of hydrolysis greater than 90% and viscosities in a 4% solution greater than 2 Pa.s. The viscosity of the prepared gel will preferably be between 2,000 and 3,000 Pa.s for facilitating spreading without the thickness of the coating being too small.

It goes without saying that the invention is not limited to the examples described herein but includes all modifications and variations within the scope of the appended claims.

What is claimed is:

1. A disposable conductive cutaneous coating for application to an area of a person's skin for use in applying electric currents for therapeutic or beauty treatment, said coating comprising a layer of a settable composition, spread over an area of skin and having substantial electrical conductivity during setting but substantially no conductivity when set, the improvement wherein the composition is a gel progressively polymerizable when brought into contact with air and comprises a terniary mixture consisting essentially of polyvinyl alcohol, ethanol and water, and a plastifier physiologically acceptable for topical application, whereby upon setting the coating is removable from the person's skin.

2. A conductive coating according to claim 1, wherein the plastifier comprises water-soluble lanolin and glycerol in proportion by weight between 4/1 and 1/1.

3. A conductive coating according to claim 2, wherein the composition comprises 15 to 30 wt % polyvinyl alcohol having a degree of hydrolysis greater than 85%, 7 to 15 wt % ethanol, 1.5 to 3 wt % water-soluble lanolin, 0.7 to 1.5 wt % glycerol, the remainder being water.

4. A conductive coating according to claim 3, wherein the composition comprises 30 wt % polyvinyl alcohol, 10 wt % ethanol, 2 wt % water-soluble lanolin, 1 wt % glycerol, and the remainder water.

5. A conductive coating according to claim 4, wherein the amount of polyvinyl alcohol in the composition is adjusted together with the amount of condensation so that the viscosity of the gel is between 2,000 and 3,000 Pa.s.

6. A conductive coating according to claim 4, wherein the polyvinyl alcohol has an ester index of about 70, and a degree of condensation such that the viscosity of a 4 wt % aqueous solution is 3 Pa.s at 20° C.

7. A conductive coating according to claim 3, wherein the amount of polyvinyl alcohol in the composition is adjusted together with the amount of condensation so that the viscosity of the gel is between 2,000 and 3,000 Pa.s.

8. A conductive coating according to claim 3, wherein the polyvinyl alcohol has an ester index of about 70, and a degree of condensation such that the viscosity of a 4 wt % aqueous solution is 3 Pa.s at 20° C.

9. A conductive coating according to claim 2, wherein the amount of polyvinyl alcohol in the composition is adjusted together with the amount of condensation so that the viscosity of the gel is between 2,000 and 3,000 Pa.s.

10. A conductive coating according to claim 2, wherein the polyvinyl alcohol has an ester index of about 70, and a degree of condensation such that the viscosity of a 4 wt % aqueous solution is 3 Pa.s at 20° C.

11. A conductive coating according to claim 1, wherein the amount of polyvinyl alcohol in the composition is adjusted together with the amount of condensation so that the viscosity of the gel is between 2,000 and 3,000 Pa.s.

12. A conductive coating according to claim 1, wherein the polyvinyl alcohol has an ester index of about 70, and a degree of condensation such that the viscosity of a 4 wt % aqueous solution is 3 Pa.s at 20° C.

13. Apparatus for cutaneous therapeutic or beauty treatment by applying pulsed electric current to facial skin, including a conductive coating adapted to be applied as a facial mask and leads connecting the conductive coating to terminals of a generator, the improvement wherein said conductive coating comprises a one-piece facial mask of a gel polymerizable in contact with air and comprising 15 to 30 wt % polyvinyl alcohol having a degree of hydrolysis greater than 85%, 5 to 15 wt % ethanol, 1.5 to 3 wt % water-soluble lanolin, 0.7 to 1.5 wt % glycerol, the remainder being water, and wherein said leads have two conductors, each of said conductors being connected to a respective conductive plate, each of said conductive plates being disposed at respective electrically insulated ends of an arcuate head clip, each of said conductive plates also bearing against the mask through a porous pad, said porous pad being soaked with a saline solution and said porous pads being locatable at the rear of the cheekbones at ear level.

14. Apparatus according to claim 13, wherein the generator is self-contained and independent.

15. Apparatus according to claim 14, wherein the generator provides voltage pulses having peak attaining 150 V, an effective intensity up to 2 mA and a recurrent frequency between 40 and 110 cycles/second.

16. A disposable conductive cutaneous coating for application to an area of a person's skin for use in applying electric currents for therapeutic or beauty treatment, said coating comprising a layer of a settable composition, spread over an area of skin and having substantial electrical conductivity only during setting, wherein said composition is a gel progressively polymerizable when brought into contact with air and comprises a terniary mixture consisting essentially of 15 to 30 wt. % polyvinyl alcohol, 5 to 15 wt. % ethanol, a plastifier physiologically acceptable for topical application, which comprises 1.5 to 3 wt. % water-soluble lanolin and 0.7 to 1.5 wt. % glycerol in a weight ratio of 4/1 and 1/1, and the balance water.

17. An apparatus for cutaneous therapeutic or beauty treatment by applying pulsed electric current to facial skin, including a conductive coating adapted to be applied as a facial mask and electrical connecting means connecting the conductive coating to terminals of a generator; said conductive coating comprising a one-piece facial mask of a gel polymerizable in contact with air and comprising 15–30 wt. % polyvinyl alcohol, 5 to 15 wt. % ethanol, 1.5 to 3 wt. % water-soluble lanolin, 0.7 to 1.5 wt. % glycerol, the remainder being water; said electrical connecting means comprising a lead connected at one end to the terminals of said generator and at the other end to two conductors, each of said two conductors being connected to a respective conductive, plate, each of said conductive plates being disposed at respective electrically insulated ends of an arcuate head clip, each of said conductive plates also bearing against the mask through a porous pad, each of said porous pads being soaked with a saline solution, and said porous pads being locatable at the rear of the cheekbones at ear level.

* * * * *